United States Patent [19]

Baba et al.

[11] Patent Number: 5,120,898
[45] Date of Patent: Jun. 9, 1992

[54] PROCESS FOR ISOMERIZING HYDROCARBONS

[75] Inventors: Shigeo Baba; Yukio Shibata; Takahiro Kawamura; Hideo Takaoka, all of Yokkaichi; Tsuguo Kimura, Yokosuka; Kazuo Kousaka, Shinagawa; Yoshihiro Minato, Chigasaki; Naruo Yokoyama, Hiroshima; Kozo Iida, Hiroshima; Tetsuya Imai, Hiroshima, all of Japan

[73] Assignee: Research Association for Utilization of Light Oil, Tokyo, Japan

[21] Appl. No.: 702,209

[22] Filed: May 15, 1991

Related U.S. Application Data

[60] Division of Ser. No. 326,418, Mar. 21, 1989, Pat. No. 5,036,035, which is a continuation-in-part of Ser. No. 15,564, Feb. 13, 1987, abandoned, which is a continuation of Ser. No. 774,231, Sep. 9, 1985, abandoned.

[30] Foreign Application Priority Data

| Sep. 10, 1984 | [JP] | Japan | 59-188206 |
| Sep. 10, 1984 | [JP] | Japan | 59-188207 |
| Dec. 26, 1984 | [JP] | Japan | 59-273481 |
| Dec. 26, 1984 | [JP] | Japan | 59-273482 |
| Mar. 25, 1985 | [JP] | Japan | 60-58229 |

[51] Int. Cl.⁵ .............................................. C07C 5/27
[52] U.S. Cl. ................................... 585/750; 585/734; 585/668; 585/671; 585/482
[58] Field of Search ............... 585/750, 734, 668, 671, 585/482

[56] References Cited

U.S. PATENT DOCUMENTS 3,032,599  5/1962  Holm et al. ............... 585/750 X
3,132,110  5/1964  Hansford .................. 585/750 X Primary Examiner—W. J. Shine
Assistant Examiner—Douglas J. McGinty
Attorney, Agent, or Firm—Wenderoth, Lind & Ponack

[57] ABSTRACT

A solid strong acid catalyst useful for hydrocarbon reactions, especially for the skeletal isomerization of paraffinic hydrocarbons is provided by supporting sulfate ($SO_4$) and at least one member selected from Group VIII metals on a support consisting of hydroxides and oxides of Group IV metals and Group III metals and mixtures thereof and then calcining and stabilizing the catalyst.

2 Claims, No Drawings

PROCESS FOR ISOMERIZING HYDROCARBONS

This is a divisional application of U.S. application Ser. No. 07/326,418, filed Mar. 21, 1989, now U.S. Pat. No. 5,036.035, which in turn is a continuation-in-part of application Ser. No. 07/015,564, filed Feb. 13, 1987, now abandoned, which in turn is a continuation Ser. No. 06/774,231, filed Sep. 9, 1985, now abandoned.

BACKGROUND OF THE INVENTION

1. Field of the Invention

This invention relates to a solid strong acid catalyst and more particularly, it is concerned with a solid strong acid catalyst in which sulfate ($SO_4$) and Group VIII metals of Periodic Table are supported on hydroxides or oxides of Group IV metals of Periodic Table and/or hydroxides or oxides of Group III metals of Periodic Table, and a process for the production of the same.

2. Description of the Prior Art

As reactions in the petroleum refining and petrochemical industry, there are catalytic cracking, catalytic reforming, hydrodesulfurization, isomerization, alkylation of aliphatic and aromatic hydrocarbons, polymerization, etc., and it has been recognized as to catalysts used for these reactions that the acid property thereof is one of important factors for reactivity. In the field of the so-called $C_1$ chemistry using methanol or synthesis gas as a raw material, wherein various studies or developments have eagerly been made lately, solid acid catalysts typical of which are metal silicates play an important role, as well known in the art.

Generally, it is considered that there is an optimum value in the solid acid strength required for a certain reaction and on the other hand, it is also known that when using "superacid" defined as a stronger acid than 100% sulfuric acid (Cf. "Superacids and Superbases" by Kozo Tanabe and Ryoji Noyori, published by Kodansha Scientific (1980)), skeletal isomerization reactions of paraffins proceeds even at room temperature. However, the solid superacid catalysts of the prior art have the drawbacks that large amounts of by-products consisting predominantly of cracked products are formed in addition to the object product and the active sites are poisoned by carbonaceous materials secondarily formed so that the catalyst life is shortened not so as to be practical. In actual fact, therefore, evaluation of the activity of the catalyst has been carried out by prolonging the contact time largely to increase the efficiency using a reaction test apparatus of closed cycle system.

SUMMARY OF THE INVENTION

It is an object of the present invention to provide a solid strong acid catalyst with long life.

It is another object of the present invention to provide a solid strong acid catalyst with less formation of by-products, in which sulfate and a Group VIII metal are supported.

It is a further object of the present invention to provide a process for the production of a solid strong acid catalyst with a lengthened life and less formation of by-products, in which sulfate and a Group VIII metal are supported.

These objects can be attained by a solid strong acid catalyst comprising sulfate ($SO_4$) and at least one selected from GROUP VIII metals, supported on at least one member selected from the group consisting of hydroxides and oxides of Group IV metals and Group III metals, and mixtures thereof, and a process for the production of a solid strong acid catalyst, which comprises incorporating at least one selected from Group VIII metals and sulfate ($SO_4$) or a precursor of sulfate ($SO_4$) in a support consisting essentially of at least one member selected from the group consisting of hydroxides and oxides of Group IV metals and Group III metals, and then calcining and stabilizing.

DETAILED DESCRIPTION OF THE INVENTION

The inventors have made various efforts to solve the problems of the prior art and consequently, have found a solid strong acid catalyst having a long life as well as a high activity for various organic reactions requiring acid catalysts and accomplished a process for the production of the same.

That is, it is found that the strong acid catalyst obtained by supporting sulfate and at least one of Group VIII metals on a support consisting of hydroxides or oxides of Group IV metals and/or hydroxides or oxides of Group III metals has a superstrong acidity and stable catalytic activity, in particular, suitable for skeletal isomerization of paraffinic hydrocarbons, production of gasoline fractions from methanol, alkylation of aliphatic and aromatic hydrocarbons and polymerization or decomposition of paraffins or olefins.

The support used in the present invention consists of at least one selected from the group consisting of hydroxides and oxides of Group IV metals and Group III metals of Periodic Table, such as hydroxides and oxides of titanium, zirconium, silicon, germanium, tin, aluminum, gallium, indium and thallium.

In the present invention, Group VIII metals of Periodic Table and sulfate ($SO_4$) or a precursor of sulfate ($SO_4$) is incorporated in the support. Group VIII metals are nickel, platinum, ruthenium, rhodium, palladium, osmium and iridium, and compounds thereof, and can be incorporated in the support in conventional manner, for example, by the impregnation method or ion exchange method. The quantity of Group VIII metals to be supported is preferably 0.01 to 10 parts by weight per 100 parts by weight of the support, since if less than 0.01 part by weight, the catalytic effect of Group VIII metals is decreased and the stability of the activity is insufficient, while if more than 10 parts by weight, the acid strength is lowered to decrease the conversion.

As the sulfate, for example, there can be used sulfuric acid with a concentration of 0.01 to 10N, preferably 0.1 to 5N and ammonium sulfate with a concentration of 0.1 to 10 mols. As the precursor of sulfate, for example, there can be used materials capable of forming sulfate after calcining, i.e. hydrogen sulfide, sulfur dioxide and sulfur- and halogen-containing compounds such as fluorosulfonic acid, sulfuryl chloride, thionyl chloride and the like.

According to the present invention, introduction of Group VIII metals and sulfate can be carried out by any of known methods. For example, a Group VIII metal is introduced into the support, which is then treated with an agent containing sulfate, calcined and stabilized, thus preparing a solid strong acid catalyst. Group VIII metals, for example, platinum can be supported by an aqueous solution of chloroplatinic acid or tetrammine platinum complex and thereafter, a sufficient catalytic property can be given by only a drying treatment prior to the treatment with a sulfate-containing agent. During the same time, as the sulfate-containing agent, sulfuric acid with a concentration of 0.01 to 10N, preferably 0.1 to 5N or ammonium sulfate with a concentration of 0.1 to 10 mols is used in a quantity of 1 to 10 times as much as the catalyst weight, and other compounds capable of forming sulfate after a calcining treatment, such as hydrogen sulfide, sulfur dioxide and sulfuryl chloride can of course be used with the similar effects.

Introduction of Group VIII metals and sulfate can be also carried out by the use of at least one sulfate of Group VIII metals. The sulfates of Group VIII metals, for example, are nickel sulfate, platinum sulfate, paradium sulfate, ruthenium sulfate and nickel ammonium sulfate. The sulfates of Group VIII metals can be supported by any method, e.g. impregnation using an aqueous solution of nickel sulfate.

After supporting a Group VIII metal, calcination in the air can be carried out at a temperature of 50° to 550° C., preferably 100° to 400° C. for 1 to 24 hours, but for the present invention, it is important to effect a calcining and stabilizing treatment at a temperature of 450° to 800° C., preferably 500° to 650° C. for 0.5 to 10 hours in an oxidizing atmosphere after the treatment with the sulfate-containing agent.

According to this procedure, a part of sulfate introduced into the support is reduced. However, the remained sulfate is incorporated in a proportion of 0.1 to 25 parts by weight to 100 parts by weight of the support to have an interaction with support materials. Thus, the catalyst is given a strong acidity. When the calcining and stabilizing treatment is carried out in a reducing atmosphere, the catalytic activity is lowered to a great extent probably due to change of the bonding state of sulfate on the Group VIII metal or compound thereof, or to reduction and decomposition thereof. This is not favourable.

In another embodiment of the present invention, the support can be subjected firstly to the treatment with a sulfate-containing agent and then to supporting of a Group VIII metal thereon a sit is or after a calcining treatment at a temperature of 50° to 600° C. After the Group VIII metal is supported, it is necessary to calcine and stabilize the catalyst at a temperature of 450° to 800° C. for 0.5 to 10 hours in an oxidizing atmosphere.

The catalyst prepared in this way is capable of exhibiting an excellent catalytic activity under flow of hydrogen. That is to say, it is considered that a Group VIII metal acts as a center of supplying active hydrogen for solid strong acid sites formed of sulfate and a metal oxide surface. Before use of this catalyst, a reduction procedure at lower than 400° C. is preferred, but is not always necessary for this catalyst. Through this procedure, there is found no generation of hydrogen sulfide, etc. due to reduction of sulfate under flowing of hydrogen. Thus, it is assumed that sulfate is firmly bound with the catalyst surface by effecting the calcining and stabilizing treatment in the final step of the process for preparing the catalyst, and a stable strong acid catalyst is thus formed.

The catalyst prepared according to the process of the present invention is useful for various reactions, in particular, isomerization of hydrocarbons. That is, various useful products can selectively be obtained by the use of the catalyst according to the present invention for skeletal isomerization of paraffinic hydrocarbons, isomerization of cyclic compounds, e.g. obtaining cyclohexane from methylcyclopentane, isomerization of aromatic compounds, e.g. obtaining p-xylene from m-xylene.

The above described isomerization reactions are preferably carried out at a reaction temperature of 400° C. or lower, since if the reaction is carried out at a temperature of higher than 400° C., in particular, in the presence of hydrogen, sulfate ($SO_4$) causing strong acid is decomposed to lower the acid strength of the catalyst and the isomerization does not proceed.

The catalyst of present invention which is highly active at a lower temperature is particularly useful for skeletal isomerization reaction of light petroleum fractions in order to get higher octane number products because the thermodynamic equilibrium of light paraffinic hydrocarbons shows that the presence of higher octane number components—highly branched paraffins—are advantageous at a lower temperature.

In the skeletal isomerization reaction described above according to the present invention, for example, a feed oil of an octane number of 60-70 containing 50 to 80% of paraffinic hydrocarbons such as n-pentane and n-hexane, known as light naphtha fractions, can selectively be converted into a useful oil as a gasoline fraction of an octane number of 80-90 in the presence of the catalyst of the present invention at a temperature of 400° C. or lower, preferably 70° to 250° C., a pressure of 1 to 50 bar, a liquid space velocity of 0.5 to 10 $hr^{-1}$ and a hydrogen to feed oil molar ratio of 1 to 10. In this case, better results can be obtained by subjecting the catalyst to a reducing treatment at a temperature of 100° to 400° C. immediately before use for the purpose of stabilizing the activity, i.e., reducing a supported metal compound to the metal and activating strong acid sites.

The following examples are given in order to illustrate the present invention in greater detail without limiting the same.

EXAMPLE 1

900 g of commercially available zirconium oxychloride (manufactured by KANTO CHEMICAL CO., LTD.) was dissolved in 7000 g of pure water and the pH was adjusted to 10 by adding a suitable amount of aqueous ammonia to form a precipitate. The precipitate was aged for a whole day and night, filtered, washed and dried to obtain 300 g of Support A ($Zr(OH)_4$).

Support A was impregnated with aqueous solutions of chloroplatinic acid, palladium chloride, nickel nitrate, ferric nitrate, cobalt nitrate, ruthenium chloride and rhodium chloride respectively, dried at 110° C. for a whole day and night, added to 650 g of 1N sulfuric acid, the excess of which was separated by filtration, and calcined at 600° C. for 3 hours to obtain Catalyst1 to 7.

500 g of titanium tetrachloride (manufactured by WAKO PURE CHEMICAL INDUSTRIES, LTD) was dissolved in 800 g of pure water and the pH was adjusted to precipitate. The precipitate was aged, filtered and dried to obtain 150 g of Support B ($Ti(OH)_4$).

700 g of aluminum nitrate (manufactured by WAKO PURE CHEMICAL INDUSTRIES, LTD) was dissolved in 950 g of pure water and the pH was adjusted to precipitate. The resulting precipitate was aged, filtered and dried to obtain 220 g of Support C ($Al(OH)_3$).

Support D ($Si(OH)_4.Zr(OH)_4$, Support E ($Ti(OH)_4.Zr(OH)_4$) and Support F ($Sn(OH)_4.Al(OH)_3$) were obtained by the coprecipitation method using water glass (manufactured by WAKO PURE CHEMICAL INDUSTRIES, LTD), zirconium oxychloride (manufactured by KANTO CHEMICAL CO., LTD), stannous chloride (manufactured by WAKO PURE CHEMICAL INDUSTRIES, LTD) and aluminum nitrate (manufactured by WAKO PURE CHEMICAL INDUSTRIES, LTD).

Supports B to F were immersed in an aqueous solution of chloroplatinic acid with such a concentration as to give 0.5 part by weight as platinum metal per 100 parts by weight of the support, dried at 110° C., added to an aqueous solution of ammonium sulfate with a concentration of 1 mol the excess of which was separated by filtration, dried at 110° C. and calcined at 600° C. for 3 hours to prepare Catalysts 8 to 12.

The solid acid strength was determined by the titration method using a Hammett indicator in a benzene solvent to obtain results as shown in Table 1.

COMPARATIVE EXAMPLE 1

Support A prepared in an analogous manner to Example 1 was immersed in an aqueous solution of chloroplatinic acid with such a concentration as to give 0.5 part by weight as platinum metal per 100 parts by weight of the support weight, dried at 110° C. and calcined at 600° C. for 3 hours to obtain Comparative Catalyst 1. The solid acid strength was determined by the titration method using a Hammett indicator in a benzene solvent to obtain results as shown in Table 1.

COMPARATIVE EXAMPLE 2

Support A prepared in an analogous manner to Example 1 was dried at 110° C., added to 1N sulfuric acid the excess of which was then separated by filtration, dried at 110° C. and then calcined at 600° C. for 3 hours to obtain Comparative Catalyst 2. The solid acid strength was determined by the titration method using a Hammett indicator in a benzene solvent to obtain results as shown in Table 1.

110° C. for a whole day and night and then calcined at 600° C. for 3 hours to prepare Catalysts 13 and 14.

Support G was immersed in aqueous solutions of palladium chloride, rhodium chloride and ruthenium chloride respectively, dried at 110° C. for a whole day and night and then calcined at 600° C. for 3 hours to prepare Catalysts 15, 16 and 17 each having 0.5 part by weight of palladium, rhodium and ruthenium per 100 parts by weight of the support.

Support G was immersed in aqueous solutions of ferric nitrate, cobalt nitrate and nickel nitrate respectively, dried at 110° C. for a whole day and night and then calcined at 600° C. for 3 hours to prepare Catalysts 18, 19 and 20 supporting each 2 parts by weight of ferric oxide, cobalt oxide and nickel oxide per 100 parts by weight of the support.

The solid acid strength was determined by the titration method using a Hammett indicator in a solvent of benzene to obtain results as shown in Table 2.

150 g of Support B of Example 1 was added to 500 ml of an aqueous solution of ammonium sulfate with a concentration of 1 mol, the excess of which was separated by filtration, dried, immersed in an aqueous solution of chloroplatinic acid with such a concentration as to give 0.5 part by weight as platinum metal to 100 parts by weight of the support, dried at 110° C. and then calcined at 600° C. for 3 hours to prepare Catalyst 21.

220 g of Supports C, D and F of Example 1 were respectively added to 500 ml of an aqueous solution of ammonium sulfate with a concentration of 2 mols, the excess of which was separated by filtration, dried, immersed in an aqueous solution of chloroplatinic acid with such a concentration as to give 0.5 part by weight as platinum metal per 100 parts by weight of the support, dried at 110° C. and calcined at 600° C. for 3 hours to prepare Catalysts 22 to 24.

The solid acid strength was determined by the titration method using a Hammett indicator in a benzene solvent to obtain results as shown in Table 2.

TABLE 1

| Catalyst No. | Composition | Amount of Group VIII Metals Supported (wt %) | Surface Area ($m^2/g$) | pKa Value of Hammett Indicator | | | | |
|---|---|---|---|---|---|---|---|---|
| | | | | $-3.0$ | $-5.6$ | $-8.2$ | $-11.4$ | $-12.7$ |
| 1 | $SO_4/Pt/ZrO_2$ | 0.5 | 80 | + | + | + | + | + |
| 2 | $SO_4/Pd/ZrO_2$ | 0.1 | 95 | + | + | + | + | + |
| 3 | $SO_4/Ni/ZrO_2$ | 9.8 | 68 | + | + | + | + | + |
| 4 | $SO_4/Fe/ZrO_2$ | 5.0 | 70 | + | + | + | + | + |
| 5 | $SO_4/Co/ZrO_2$ | 5.0 | 70 | + | + | + | + | + |
| 6 | $SO_4/Rh/ZrO_2$ | 0.01 | 88 | + | + | + | + | + |
| 7 | $SO_4/Rh/ZrO_2$ | 0.2 | 90 | + | + | + | + | + |
| 8 | $SO_4Pt/TiO_2$ | 0.5 | 65 | + | + | + | + | + |
| 9 | $SO_4/Pt/Al_2O_3$ | 0.5 | 153 | + | + | + | + | + |
| 10 | $SO_4/Pt/SiO_2.ZrO_2$ | 0.5 | 120 | + | + | + | + | + |
| 11 | $SO_4/Pt/TiO_2.ZrO_2$ | 0.5 | 95 | + | + | + | + | + |
| 12 | $SO_4Pt/SnO_2.Al_2O_3$ | 0.5 | 130 | + | + | + | + | + |
| Comparative Catalysts | | | | | | | | |
| 1 | $Pt/ZrO_2$ | 0.5 | 35 | ± | − | − | − | − |
| 2 | $SO_4/ZrO_2$ | — | 100 | + | + | + | + | + |

Note: Examination results of discoloration point in benzene (+: discoloration; ± some discoloration; − no discoloration) Hammett indicator: −3.0: dicinnamalacetone; −5.6: benzalacetophenone; −8.2: anthraquinone; −11.4: p-nitrotoluene; −12.7: p-nitrochlorotoluene

EXAMPLE 2

300 g of Support A of Example 1 was added to 650 g of 1N sulfuric acid the excess of which was separated by filtaration, dried at 110° C. for one day and night to give Support G and then calcined at 600° C. for 3 hours to prepare Support H.

Supports G and H were respectively immersed in an aqueous solution of chloroplatinic acid with such a concentration as to give 0.5 part by weight as platinum metal to 100 parts by weight of the support, dried at

TABLE 2

| Catalyst No. | Composition | pKa Value of Hammett Indicator* | | | | |
|---|---|---|---|---|---|---|
| | | $-3.0$ | $-5.6$ | $-8.2$ | $-11.4$ | $-12.7$ |
| 13 | $Pt/SO_4/ZrO_2$ | + | + | + | + | + |
| 14 | $Pt/SO_4/ZrO_2$ | + | + | + | + | + |

The solid acid strength was determined by the titration method using a Hammett indicator in a solvent of benzene to obtain results as shown in Table 3.

TABLE 2-continued

| Catalyst | pKa Value of Hammett Indicator* |
| --- | --- |

| No. | Composition | -3.0 | -5.6 | -8.2 | -11.4 | -12.7 |
| --- | --- | --- | --- | --- | --- | --- |
| 15 | Pd/SO$_4$/ZrO$_2$ | + | + | + | + | + |
| 16 | Rh/SO$_4$/ZrO$_2$ | + | + | + | + | + |
| 17 | Ru/SO$_4$/ZrO$_2$ | + | + | + | + | + |
| 18 | Fe$_2$O$_3$/SO$_4$/ZrO$_2$ | + | + | + | + | + |
| 19 | CoO/SO$_4$/ZrO$_2$ | + | + | + | + | + |
| 20 | NiO/SO$_4$/ZrO$_2$ | + | + | + | + | + |
| 21 | Pt/SO$_4$/TiO$_2$ | + | + | + | + | + |
| 22 | Pt/SO$_4$/Al$_2$O$_3$ | + | + | + | + | + |
| 23 | Pt/SO$_4$/SiO$_2$.ZrO$_2$ | + | + | + | + | + |
| 24 | Pt/SO$_4$/SnO$_2$.Al$_2$O$_3$ | + | + | + | + | + |

Note: *same as in Table 1

TABLE 3

| Catalyst No. | Composition | Amount of Group VIII metals Supported (wt %) | Surface Area (m$^2$g) | Calcining Temperature (°C.) | Supported Sulfate (SO$_4$) (wt %) | pKa Value of Hammett Indicator* | | | | |
| --- | --- | --- | --- | --- | --- | --- | --- | --- | --- | --- |
| | | | | | | -3.0 | -5.6 | -8.2 | -11.4 | -12.7 |
| 25 | NiSO$_4$/ZrO$_2$ | 5.0 | 95 | 550 | 6.9 | + | + | + | + | + |
| 26 | NiSO$_4$/ZrO$_2$ | 5.0 | 82 | 600 | 7.2 | + | + | + | + | + |
| 27 | NiSO$_4$/ZrO$_2$ | 5.0 | 86 | 650 | 7.0 | + | + | + | + | + |
| 28 | NiSO$_4$/ZrO$_2$ | 5.0 | 64 | 700 | 5.1 | + | + | + | + | + |
| 29 | NiSO$_4$/ZrO$_2$ | 5.0 | 14 | 800 | 1.2 | + | + | + | + | + |
| 30 | NiSO$_4$/TiO$_2$ | 5.0 | 59 | 650 | 4.2 | + | + | + | + | + |
| 31 | NiSO$_4$/Al$_2$O$_3$.ZrO$_2$ | 5.0 | 120 | 650 | 7.2 | + | + | + | + | + |
| 32 | PdSO$_4$/ZrO$_2$ | 0.5 | 103 | 575 | 0.5 | + | + | + | + | + |
| 33 | Pt/SO$_4$/ZrO$_2$ | 0.01 | 85 | 575 | 0.1 | + | + | + | + | + |
| 34 | Rh/SO$_4$/ZrO$_2$ | 0.5 | 95 | 575 | 0.3 | + | + | + | + | + |

Note: *same as in Table 1

EXAMPLE 3

Support A of Example 1 was immersed in an aqueous solution of nickel sulfate with such a concentration as to give 5.0 parts by weight as nickel metal to 100 parts by weight of the support, dried at 110° C. for a whole day and night and then calcined at 550° C., 600° C., 650° C., 700° C. and 800° C. for 3 hours to prepare Catalysts 25 to 29.

Support I (Al(OH)$_3$.Zr(OH)$_4$) was prepared by the conventional coprecipitation method using aluminum nitrate (Manufactured by WAKO PURE CHEMICAL INDUSTRIES, LTD) and zirconium oxychloride (manufactured by KANTO CHEMICAL CO., LTD). Support B of Example 1 and Support I were immersed in an aqueous solution of nickel sulfate with such a concentration as to give 5.0 parts by weight as nickel metal to 100 parts by weight of the support, dried at 110° C. for a whole day and night and then calcined at 650° C. for 3 hours to prepare Catalysts 30 and 31.

Support A of Example 1 was immersed in an aqueous solution of palladium sulfate, aqueous sulfuric acid solution of chloroplatinic acid and aqueous sulfuric acid solution of rhodium chloride, dried at 110° C. for a whole day and night and then calcined at 575° C. for 3 hours to prepare Catalysts 32 to 34 supporting respectively 0.5, 0.01 and 0.5 part by weight of palladium, platinum and rhodium pr 100 parts by weight of the support.

EXAMPLE 4

300 g of Support A of Example 1 was immersed in an aqueous solution of chloroplatinic acid, palladium chloride, nickel nitrate, ferric nitrate, cobalt nitrate, ruthenium chloride or rhodium chloride, dried at 110° C. for a whole day and night, added to 500 ml of a solution of sulfuryl chloride (reagent chemical grade, manufactured by WAKO PURE CHEMICAL INDUSTRIES, LTD.), dried at 110° C. for a whole day and night and then calcined at 600° C. for 3 hours to prepare Catalysts 35 to 41.

Supports B and C of Example 1 were immersed in an aqueous solution of chloroplatinic acid with such a concentration as to give 0.5 part by weight as platinum metal to 100 parts by weight of the support, dried at 110° C., added to a solution of thionyl chloride (made by WAKO PURE CHEMICAL INDUSTRIES, LTD.), dried at 110° C. for a whole day and night and then calcined at 600° C. for 3 hours to prepare Catalysts 42 and 43.

Supports D to F of Example 1 were immersed in an aqueous solution of chloroplatinic acid with such a concentration as to give 0.5 part by weight as platinum metal to 100 parts by weight of the support, dried at 110° C., added to a solution of commercially available fluorosulfonic acid (manufactured by WAKO PURE CHEMICAL INDUSTRIES, LTD.), the excess of which was separated by filtration, and then calcined at 600° C. for 3 hours to prepare Catalysts 44 to 46.

The solid acid strength thereof was measured by the titration method using a Hammett indicator in a solvent of benzene to obtain results as shown in Table 4.

COMPARATIVE EXAMPLE 3

Support A of Example 1 was immersed in an aqueous solution of commercially available sulfuryl chloride (manufactured BY WAKO PURE CHEMICAL INDUSTRIES, LTD.), dried at 110° C. for a whole day and night and then calcined at 600° C. for 3 hours to prepare Comparative Catalyst 3. The solid acid strength was measured by the titration method using a Hammett indicator in a benzene solvent to obtain results as shown in Table 4.

TABLE 4

| Catalyst No. | Composition | Amount of Group VIII Metals Supported (wt %) | Surface Area (m$^2$g) | pKa Value of Hammett Indicator* | | | | |
| --- | --- | --- | --- | --- | --- | --- | --- | --- |
| | | | | -3.0 | -5.6 | -8.2 | -11.4 | -12.7 |
| 35 | SO$_2$Cl$_2$**/Pt/ZrO$_2$ | 0.5 | 90 | + | + | + | + | + |

TABLE 4-continued

| Catalyst No. | Composition | Amount of Group VIII Metals Supported (wt %) | Surface Area (m²/g) | pKa Value of Hammett Indicator* −3.0 | −5.6 | −8.2 | −11.4 | −12.7 |
|---|---|---|---|---|---|---|---|---|
| 36 | SO$_2$Cl$_2$/Pd/ZrO$_2$ | 0.1 | 88 | + | + | + | + | + |
| 37 | SO$_2$Cl$_2$/Ni/ZrO$_2$ | 9.8 | 72 | + | + | + | + | + |
| 38 | SO$_2$Cl$_2$/Fe/ZrO$_2$ | 5.0 | 75 | + | + | + | + | + |
| 39 | SO$_2$Cl$_2$/Co/ZrO$_2$ | 5.0 | 75 | + | + | + | + | + |
| 40 | SO$_2$Cl$_2$/Ru/ZrO$_2$ | 0.01 | 93 | + | + | + | + | + |
| 41 | SO$_2$Cl$_2$/Rh/ZrO$_2$ | 0.2 | 105 | + | + | + | + | + |
| 42 | SOCl$_2$/Pt/TiO$_2$ | 0.5 | 70 | + | + | + | + | + |
| 43 | SOCl$_2$/Pt/Al$_2$O$_3$ | 0.5 | 122 | + | + | + | + | + |
| 44 | FSO$_4$**/Pt/SiO$_2$.ZrO$_2$ | 0.5 | 78 | + | + | + | + | + |
| 45 | FSO$_4$/Pt/SiO$_2$.ZrO$_2$ | 0.5 | 60 | + | + | + | + | + |
| 46 | FSO$_4$/Pt/SnO$_2$.Al$_2$O$_3$ | 0.5 | 83 | + | + | + | + | + |
| Comparative Catalyst 3 | SO$_2$Cl$_2$/ZrO$_2$ | | 100 | + | + | + | + | + |

Note:
*same as in Table 1
**"SO$_2$Cl$_2$" or "FSO$_4$" is finally converted in to "SO$_4$".

EXAMPLE 5

300 g of Support A of Example 1 was immersed in 600 ml of a solution of commercially available sulfuryl chloride (reagent chemical grade, manufactured by WAKO PURE CHEMICAL INDUSTRIES, LTD.), dried at 110° C. for a whole day and night and then calcined at 600° C. for 3 hours to prepare Support J.

Support I and J were immersed respectively in an aqueous solution of chloroplatinic acid with such a concentration as to give 0.5 part by weight as platinum metal to 100 parts by weight of the support, dried at 110° C. for a whole day and night and then calcined at 600° C. for 3 hours to prepare Catalysts 47 and 48.

Support I was immersed in aqueous solutions of palladium chloride, rhodium chloride and ruthenium chloride respectively, dried at 110° C. for a whole day and night and then calcined at 600° C. for 3 hours to prepare Catalysts 49 to 51 each supporting 0.5 part by weight of palladium, rhodium and ruthenium per 100 parts by weight of the support.

Furthermore, Support I was immersed in aqueous solutions of ferric nitrate, cobalt nitrate and nickel nitrate respectively, dried at 110° C. for a whole day and night and then calcined at 600° C. for 3 hours, thus preparing Catalysts 52 to 54 supporting respectively 2 parts by weight of iron oxide, cobalt oxide and nickel oxide per 100 parts by weight of the support.

150 g of Support B and 220 g of Support C of Example 1 were introduced into 500 ml of a solution of thionyl chloride (commercially available, manufactured by WAKO PURE CHEMICAL INDUSTRIES, LTD.), respectively, dried, then immersed in an aqueous solution of chloroplatinic acid with such a concentration as to give 0.5 part by weight as platinum metal, dried at 110° C. for a whole day and night and then calcined at 600° C. for 3 hours to prepare Catalysts 55 and 56.

Supports D and F of Example 1 were respectively introduced into a solution of commercially available fluorosulfonic acid (made by WAKO PURE CHEMICAL INDUSTRIES, LTD), the excess of which was separated by filtration, dried at 110° C. immersed in an aqueous solution of chloroplatinic acid with such a concentration as to give 0.5 part by weight as platinum metal to 100 parts by weight of the support, dried at 110° C. for a whole day and night and then calcined at 600° C. for 3 hours to prepare Catalysts 57 and 58.

The solid acid strength thereof was determined by the titration method using a Hammett indicator in a benzene solvent to obtain results as shown in Table 5.

TABLE 5

| Catalyst No. | Composition | pKa Value of Hammett Inidcator* −3.0 | −5.6 | −8.2 | −11.4 | −12.7 |
|---|---|---|---|---|---|---|
| 47 | Pt/SO$_2$Cl$_2$**/ZrO$_2$ | + | + | + | + | + |
| 48 | Pt/SO$_2$Cl$_2$/ZrO$_2$ | + | + | + | + | + |
| 49 | Pd/SO$_2$Cl$_2$/ZrO$_2$ | + | + | + | + | + |
| 50 | Rh/SO$_2$Cl$_2$/ZrO$_2$ | + | + | + | + | + |
| 51 | Ru/SO$_2$Cl$_2$/ZrO$_2$ | + | + | + | + | + |
| 52 | Fe$_2$O$_3$/SO$_2$Cl$_2$/ZrO$_2$ | + | + | + | + | + |
| 53 | CoO/SO$_2$Cl$_2$/ZrO$_2$ | + | + | + | + | + |
| 54 | NiO/SO$_2$Cl$_2$/ZrO$_2$ | + | + | + | + | + |
| 55 | Pt/SOCl$_2$/TiO$_2$ | + | + | + | + | + |
| 56 | Pt/SOCl$_2$/Al$_2$O$_3$ | + | + | + | + | + |
| 57 | Pt/FSO$_4$**/SiO$_2$.ZrO$_2$ | + | + | + | + | + |
| 58 | Pt/FSO$_4$/SnO$_2$.Al$_2$O$_3$ | + | + | + | + | + |

Note:
*same as in Table 1
**"SO$_2$Cl$_2$" or "FSO$_4$" is finally converted into "SO$_4$".

EXAMPLE 6

Skeletal Isomerization of n-Pentane

Catalysts 1, 13, 26, 27, 29, 35 and 47 prepared in Examples 1 to 5 and Comparative Catalysts 1 to 3 prepared in Comparative Examples 1 to 3 were respectively shaped in pellets with a diameter of 0.59–1.00 mm. Using these catalysts, hydroisomerization reaction of n-pentane as carried out in a high pressure flow reactor with a length of 22 cm and inner diameter of 1 cm under the following reaction conditions:

| | |
|---|---|
| Temperature | 200° C. |
| Total Pressure | 10 bar |
| H$_2$/n-Pentane Molar Ratio | 5/1 mol/mol |
| Liquid Space Velocity | 1.5 ml n-pentane/ml catalyst/hr |

The composition of the reactor outlet gas was continuously analyzed by gas chromatography to obtain results shown in Table 6. It will clearly be understood from Table 6 that the catalysts prepared according to the present invention are excellent catalysts having higher activities for the skeletal isomerization of n-pentane and longer catalyst life, which result from the presence of Group VIII metals and sulfate.

TABLE 6

| | Catalyst No. | | | | | | | Comparative Catalyst | | |
|---|---|---|---|---|---|---|---|---|---|---|
| | 1 | 13 | 26 | 27 | 29 | 35 | 47 | 1 | 2 | 3* |
| | | | Composition | | | | | | | |
| | $SO_4/Pt/ZrO_2$ | $Pt/SO_4/ZrO_2$ | $NiSO_4/ZrO_2$ | | | $SO_2Cl_2*/Pt/ZrO_2$ | $Pt/SO_2Cl_2*/ZrO_2$ | $Pt/ZrO_2$ | $SO_4/ZrO_2$ | $SO_2Cl_2/ZrO_2$ |
| Reactor Outlet Gas Composition (wt %) | | | | | | | | | | |
| after 5 hrs | | | | | | | | | | |
| methane, ethane, propane, i-butane, n-butane | 3 | 7 | 4 | 3 | 3 | 2 | 2 | 0 | 1 | 1 |
| i-pentane | 66 | 60 | 63 | 60 | 67 | 66 | 66 | 0 | 6 | 6 |
| n-pentane | 29 | 30 | 31 | 35 | 29 | 30 | 30 | 100 | 93 | 93 |
| i-hexane, n-hexane, etc. | 2 | 3 | 2 | 2 | 1 | 2 | 2 | 0 | 0 | 0 |
| after 10 hrs | | | | | | | | | | |
| methane, ethane, propane, i-butane, n-butane | 5 | 6 | 4 | 3 | 3 | 2 | 2 | 0 | 0 | 0 |
| i-pentane | 66 | 60 | 62 | 60 | 65 | 67 | 65 | 0 | 4 | 2 |
| n-pentane | 26 | 32 | 32 | 35 | 31 | 29 | 31 | 100 | 96 | 98 |
| i-hexane, n-hexane, etc. | 3 | 2 | 2 | 2 | 1 | 2 | 2 | 0 | 0 | 0 |
| after 16 hrs | | | | | | | | | | |
| methane, ethane, propane, i-butane, n-butane | 6 | 3 | 3 | 3 | 3 | 3 | 1 | 0 | 0 | 0 |
| i-pentane | 66 | 63 | 62 | 60 | 64 | 66 | 64 | 0 | 3 | 2 |
| n-pentane | 25 | 32 | 33 | 35 | 32 | 29 | 33 | 100 | 97 | 98 |
| i-hexane, n-hexane, etc. | 3 | 2 | 2 | 2 | 1 | 2 | 2 | 0 | 0 | 0 |

Note: *"$SO_2Cl_2$" is finally converted into $SO_4$.

EXAMPLE 7

Skeletal Isomerization of n-Pentane

Hydroisomerization reaction of n-pentane was carried out using Catalysts 2, 3, 6 and 7 under the similar reaction conditions to Example 6. The results are shown in Table 7.

| | |
|---|---|
| Temperature | 180, 200, 220 and 250° C. |
| Total Pressure | 5, 10 and 15 bar |
| $H_2$/n-Hexane Molar Ratio | 5/1 mol/mol |
| Liquid Space Velocity | 0.38, 0.75, 1.0, 1.5 and 2.0 ml n-hexane/ml catalyst/hr |

TABLE 7

| Catalyst No. | Composition | Reactor Outlet Gas Composition (wt %) | | | |
|---|---|---|---|---|---|
| | | Methane, Ethane, Propane, Butane | i-Pentane | n-Pentane | Hexane, etc. |
| 2 | $SO_4/Pd/ZrO_2$ | 4 | 68 | 25 | 3 |
| 3 | $SO_4/Ni/ZrO_2$ | 4 | 65 | 29 | 2 |
| 6 | $SO_4/Ru/ZrO_2$ | 0.5 | 34 | 65 | 0.5 |
| 7 | $SO_4/Rh/ZrO_2$ | 11 | 55 | 31 | 3 |

EXAMPLE 8

Skeletal Isomerization of n-Hexane

Using Catalysts 1 and 35, each being shaped in pellets with a diameter of 0.59–1.00 mm, hydroisomerization reaction of n-hexane was carried out in a high pressure flow reactor with a length of 22 cm and inner diameter of 1 cm under the following reaction conditions. Before the reaction, the catalysts were subjected to reduction with hydrogen at 300° C. for 2 hours to stabilize the catalytic activity. The amounts of sulfate supported on Catalysts 1 and 35 were 6.5 and 18.5% by weight on the fresh catalysts, and 6.3 and 17.2% by weight on the used catalysts, respectively.

The composition of the reactor outlet gas was analyzed by gas chromatography to obtain results as shown in Tables 8 and 9, in which:

Total Conversion (%) =

100 − Outlet Gas Composition of Unreacted n-Hexane (wt %)

Isomer Selectivity (%) =

$$\frac{\text{Ratio of Branched Hexane in Outlet Gas Composition (wt \%)}}{100 - \text{Outlet Gas Composition of Unreacted n-Hexane (wt \%)}} \times 100$$

TABLE 8

| Catalyst 1 | | | | | | | | | | | | |
|---|---|---|---|---|---|---|---|---|---|---|---|---|
| Reaction Temperature (°C.) | 200 | 200 | 200 | 200 | 200 | 200 | 200 | 200 | 180 | 200 | 220 | 250 |
| Total Pressure (bar) | 10 | 10 | 10 | 10 | 10 | 5 | 10 | 15 | 10 | 10 | 10 | 10 |
| Liquid Space Velocity ($h^{-1}$) | 0.38 | 0.75 | 1.0 | 1.5 | 2.0 | 1.5 | 1.5 | 1.5 | 1.5 | 1.5 | 1.5 | 1.5 |
| Reactor Outlet Gas | | | | | | | | | | | | |

TABLE 8-continued

| Catalyst 1 | | | | | | | | | | | | |
|---|---|---|---|---|---|---|---|---|---|---|---|---|
| Composition (wt %) | | | | | | | | | | | | |
| methane, ethane, propane, i-butane, n-butane, i-pentane, n-pentane | 6.9 | 3.8 | 2.7 | 2.3 | 1.3 | 1.3 | 2.3 | 2.5 | 0.8 | 2.3 | 4.5 | 18.1 |
| 2,2-dimethylbutane | 20.2 | 14.2 | 9.7 | 8.3 | 4.2 | 3.1 | 8.3 | 9.2 | 5.9 | 8.3 | 8.5 | 10.6 |
| 2,3-dimethylbutane | 9.8 | 10.8 | 10.9 | 10.7 | 9.6 | 7.7 | 10.7 | 10.9 | 10.0 | 10.7 | 10.1 | 8.5 |
| 2-methylpentane | 31.4 | 34.8 | 36.1 | 34.5 | 31.5 | 25.7 | 34.5 | 35.1 | 32.7 | 34.5 | 34.2 | 28.9 |
| 3-methylpentane | 18.5 | 20.7 | 21.5 | 20.6 | 18.4 | 15.5 | 20.6 | 20.4 | 18.9 | 20.6 | 21.2 | 18.2 |
| n-hexane | 12.8 | 15.3 | 18.6 | 23.0 | 34.2 | 45.9 | 23.0 | 21.2 | 30.9 | 23.0 | 20.9 | 15.4 |
| others | 0.3 | 0.5 | 0.6 | 0.7 | 0.8 | 0.8 | 0.7 | 0.6 | 0.8 | 0.7 | 0.6 | 0.2 |
| Total Conversion (%) | 87.2 | 84.7 | 81.4 | 77.0 | 65.8 | 54.1 | 77.0 | 78.8 | 69.1 | 77.0 | 79.1 | 84.6 |
| Isomer Selectivity (%) | 91.6 | 95.0 | 96.1 | 96.2 | 96.8 | 96.1 | 96.2 | 95.9 | 97.7 | 96.2 | 93.6 | 78.3 |

TABLE 9

| Catalyst 35 | | | | | | | | | | | | |
|---|---|---|---|---|---|---|---|---|---|---|---|---|
| Reaction Temperature (°C.) | 200 | 200 | 200 | 200 | 200 | 200 | 200 | 200 | 180 | 200 | 220 | 250 |
| Total Pressure (bar) | 10 | 10 | 10 | 10 | 10 | 5 | 10 | 15 | 10 | 10 | 10 | 10 |
| Liquid Space Velocity (h$^{-1}$) | 0.38 | 0.75 | 1.0 | 1.5 | 2.0 | 1.5 | 1.5 | 1.5 | 1.5 | 1.5 | 1.5 | 1.5 |
| Reactor Outlet Gas Composition (wt %) | | | | | | | | | | | | |
| methane, ethane, propane, i-butane, n-butane, i-pentane, n-pentane | 6.5 | 4.1 | 3.3 | 2.2 | 1.2 | 1.1 | 2.2 | 3.1 | 0.6 | 2.2 | 6.3 | 20.2 |
| 2,2-dimethylbutane | 21.0 | 13.8 | 10.2 | 9.5 | 4.2 | 3.1 | 9.5 | 9.6 | 6.3 | 9.5 | 8.0 | 9.2 |
| 2,3-dimethylbutane | 10.2 | 10.5 | 10.9 | 11.0 | 10.1 | 7.1 | 11.0 | 10.2 | 10.4 | 11.0 | 10.0 | 6.3 |
| 2-methylpentane | 31.2 | 39.2 | 36.3 | 36.1 | 30.8 | 26.1 | 36.1 | 35.2 | 31.5 | 36.1 | 32.7 | 28.3 |
| 3-methylpentane | 18.3 | 20.0 | 20.5 | 21.6 | 18.0 | 15.7 | 21.6 | 20.9 | 19.0 | 21.6 | 20.3 | 19.2 |
| n-hexane | 12.0 | 15.8 | 18.0 | 18.9 | 35.0 | 46.0 | 18.9 | 20.3 | 31.1 | 18.9 | 22.0 | 16.3 |
| others | 0.8 | 0.6 | 0.8 | 0.6 | 0.7 | 0.9 | 0.6 | 0.7 | 0.8 | 0.6 | 0.7 | 0.5 |
| Total Conversion (%) | 88.0 | 84.2 | 82.0 | 81.1 | 65.0 | 54.0 | 81.1 | 79.7 | 68.9 | 81.1 | 78.0 | 83.7 |
| Isomer Selectivity (%) | 91.7 | 94.4 | 95.0 | 96.4 | 97.0 | 96.3 | 96.4 | 95.2 | 98.0 | 96.4 | 91.0 | 75.3 |

EXAMPLE 9

Isomerization of Hydrocarbons 200 mg of each of Catalysts 1, 2, 26, 35, 36 and 37 was packed in a pulse reactor and isomerization reaction was carried out in a helium stream by feeding 1 ml of N$_2$ gas containing 10% of n-butane, 1 μl of liquid methylcyclopentane or liquid m-xylene, thus obtaining results shown in Table 10, in which the ratios of conversion, decomposition and isomerization are defined as follows:

Total Conversion (%) = 100 −

Outlet Gas Composition of Unreacted Feed Hydrocarbons (wt %)

Decomposition (%) =

$$\frac{\text{Ratio of Hydrocarbons with less Carbons than Feed Hydrocarbons in Outlet Gas Composition (wt \%)}}{100 - \text{Outlet Gas Composition of Feed Hydrocarbons (wt \%)}} \times 100$$

Isomerization (%) =

$$\frac{\text{Ratio of Isomers of Feed Hydrocarbons in Outlet Gas Composition (wt \%)}}{100 - \text{Outlet Gas Composition of Unreacted Feed Hydrocarbons (wt \%)}}$$

TABLE 10

| Catalyst No. | Feed Hydrocarbons | Reaction Temperature (°C.) | Conversion (%) | Decomposition (%) | Isomerization (%) |
|---|---|---|---|---|---|
| 1 | n-butane | 200 | 60.8 | 31.1 | 62.3 |
|  | methylcyclopentane | 200 | 24.0 | 8.3 | 69.2 |
|  | m-xylene | 150 | 45.6 | 53.9 | 32.5 |
| 2 | n-butane | 200 | 53.0 | 20.8 | 72.1 |
|  | methylcyclopentane | 200 | 23.4 | 7.7 | 71.4 |
|  | m-xylene | 150 | 39.1 | 43.5 | 44.0 |
| 26 | n-butane | 200 | 57.2 | 25.7 | 67.1 |
|  | methylcyclopentane | 200 | 24.6 | 7.3 | 68.3 |
|  | m-xylene | 150 | 34.2 | 27.5 | 56.7 |
| 35 | n-butane | 200 | 55.4 | 28.3 | 58.6 |
|  | methylcyclopentane | 200 | 22.7 | 10.2 | 67.7 |
|  | m-xylene | 150 | 38.3 | 50.3 | 34.9 |
| 36 | n-butane | 200 | 58.2 | 18.8 | 70.0 |
|  | methylcyclopentane | 200 | 23.9 | 8.0 | 68.2 |
|  | m-xylene | 150 | 42.1 | 42.1 | 46.0 |
| 37 | n-butane | 200 | 36.3 | 20.5 | 70.3 |
|  | methylcyclopentane | 200 | 20.5 | 3.2 | 72.9 |
|  | m-xylene | 150 | 30.0 | 38.0 | 48.3 |

EXAMPLE 10

Cracking of n-Pentane 200 mg of each powder of Catalysts 13 to 20, 32 to 34 and 47 to 54 was packed in a pulse reactor and cracking reaction of n-pentane was carried by feeding 1 μl of n-pentane to the reactor at 300° C. in helium stream. The out-oet gas composition of the pulse reactor was analyzed by gas chromatography to obtain results shown in Table 11:

TABLE 11

| Catalyst No. | Reactor Outlet Gas Composition (wt %) | | | |
|---|---|---|---|---|
| | Propane, Butane | i-Pentane | n-Pentane | Hexane and Others |
| 13 | 87 | 6 | 6 | 1 |
| 14 | 83 | 4 | 12 | 1 |
| 15 | 73 | 9 | 17 | 1 |
| 16 | 85 | 6 | 8 | 1 |
| 17 | 77 | 7 | 15 | 1 |
| 18 | 77 | 8 | 14 | 1 |
| 19 | 78 | 8 | 13 | 1 |
| 20 | 78 | 8 | 13 | 1 |
| 32 | 87 | 5 | 7 | 1 |
| 33 | 30 | 42 | 22 | 6 |
| 34 | 83 | 6 | 10 | 1 |
| 47 | 90 | 5 | 5 | 0 |
| 48 | 85 | 4 | 10 | 1 |
| 49 | 76 | 8 | 15 | 1 |
| 50 | 84 | 7 | 8 | 1 |
| 51 | 79 | 7 | 13 | 1 |
| 52 | 75 | 9 | 15 | 1 |
| 53 | 80 | 7 | 12 | 1 |
| 54 | 78 | 8 | 13 | 1 |

EXAMPLE 11

Alkylation of Hydrocarbons 60 g of each of Catalysts 13 and 47 was charged in an autoclave of 300 ml, into which a mixed liquid of isobutane and cis-2-butene (isobutane to cis-2-butene weight ratio:10:1) was introduced in an amount of 1.5 times the weight of the catalyst, and after closing the reaction system, the mixture was reacted at a reaction temperature of 60° C. and a pressure of 16 kg/cm²G for 5 hours. After the reaction, the product was taken and analyzed to obtain results as shown in Table 12:

TABLE 12

| | Catalyst 13 | Catalyst 47 |
|---|---|---|
| Conversion of cis-2-Butene | 93 | 94 |
| Selectivity (wt %) | | |
| $C_5^+$ fraction/Reacted cis-2-Butene | 205 | 209 |
| $C_8$ fraction/$C_5^+$ fraction | 53 | 54 |
| Trimethylpentane/$C_8$ fraction | 67 | 69 |

EXAMPLE 12

$Zr(OH)_4 \cdot Al(OH)_3$ powder ($ZrO_2:Al_2O_3$ weight ratio=75:25) was prepared by the coprecipitation method using zirconium oxychloride and aluminum nitrate. The resulting powder was calcined at 300° C., immersed in an aqueous solution of chloroplatinic acid with such a concentration as to give 0.5 part by weight as platinum metal to 100 parts by weight of the support, and dried at 110° C.

The thus obtained powder was introduced into an aqueous solution of ammonium sulfate with a concentration of 2 mols, the excess of which was separated by filtration, and then calcined at 550° C. for 3 hours to prepare Catalyst 59. On the other hand, the same powder was introduced into a solution of sulfuryl chloride commercially available (reagent chemical grade, manufactured by WAKO PURE CHEMICAL INDUSTRIES, LTD.) instead of the aqueous solution of ammonium sulfate, dried at 110° C. for a whole day and night and calcined at 620° C. for 3 hours to prepare Catalyst 60.

300 g of Support A of Example 1 was previously calcined at 300° C. to form $ZrO_2$. 100 g of this powder was introduced into 1000 g of 0.5N sulfuric acid, the excess of which was separated by filtration, and dried at 110° C. for a whole day and night to prepare Support K, while this powder as similarly introduced into a solution of commercially available sulfuryl chloride (reagent chemical grade, manufactured by Wako Junyaku KK) and dried at 110° C. for a whole day and night to prepare Support L.

Supports K and L were respectively immersed in an aqueous solution of chloroplatinic acid with such a concentration as to give 0.1, 0.5 or 2 parts by weight as platinum metal to 100 parts by weight of the support, dried at 110° C. for a whole day and night and then calcined at 575° C. for 3 hours to prepare respectively Catalyst 61 (Pt 0.01 part by weight), Catalyst 62 (Pt 0.05 part by weight), Catalyst 63 (Pt 2 parts by weight), Catalyst 64 (Pt 0.01 part by weight), Catalyst 65 (Pt 0.05 part by weight) and Catalyst 66 (Pt 2 parts by weight).

Catalysts 59 to 66 were respectively packed in a quantity of 200 mg in a pulse reactor and isomerization reaction of n-butane was then carried out by feeding 1 ml of $N_2$ gas containing 10% of n-butane to the reactor in helium stream.

The composition of the outlet gas of the pulse reactor was analyzed by gas chromatography to obtain results as shown in Table 13, in which the ratios of conversion, decomposition and isomerization are defined in an analogous manner to Example 9.

TABLE 13

| Catalyst No. | Composition | Reaction Temperature (°C.) | Conversion (%) | Decomposition (%) | Isomerization (%) |
|---|---|---|---|---|---|
| 59 | $SO_4/Pt(0.5)/ZrO_2.Al_2O_3$ | 200 | 25.5 | 7.8 | 68.0 |
| | | 300 | 51.6 | 32.7 | 59.7 |
| 60 | $SO_2Cl_2*/Pt(0.5)/ZrO_2.Al_2O_3$ | 200 | 23.4 | 6.8 | 70.3 |
| 61 | $Pt(0.01)/SO_4/ZrO_2.Al_2O_3$ | 200 | 54.1 | 21.0 | 71.8 |
| 62 | $Pt(0.05)/SO_4/ZrO_2.Al_2O_3$ | 200 | 58.0 | 26.1 | 67.5 |
| 63 | $Pt(2)/SO_4/ZrO_2.Al_2O_3$ | 200 | 61.5 | 31.5 | 63.0 |
| 64 | $Pt(0.01)/SO_2Cl_2/ZrO_2.Al_2O_3$ | 200 | 53.2 | 19.3 | 72.0 |
| 65 | $Pt(0.05)/SO_2Cl_2/ZrO_2.Al_2O_3$ | 200 | 60.3 | 23.3 | 68.3 |
| 66 | $Pt(2)/SO_2Cl_2/ZrO_2.Al_2O_3$ | 200 | 50.4 | 30.5 | 62.9 |

Note: *"$SO_2Cl_2$" is finally converted into "$SO_4$".

EXAMPLE 13

10 g of Support A of Example 1 was immersed in an aqueous solution of chloroplatinic acid with such a concentration as to give 0.5 part by weight as platinum metal to 100 parts by weight of the support, dried at 110° C. for a whole day and night, then treated with $N_2$ gas containing 20% of $SO_2$ flowing at a rate of 50 Nl.hr at 300° C. for 3 hours and calcined at 550° C. for 1 to prepare Catalyst 67.

200 mg of Catalyst 67 was packed in a pulse reactor and isomerization reaction of n-butane was then carried out by feeding 1 ml of $N_2$ gas containing 10% of n-butane to the pulse reactor at 300° C. in helium stream.

The outlet gas of the pulse reactor was subjected to analysis by gas chromatography to obtain a conversion of 52.0% and isomerization of 60.5% (defined similarly to Example 9).

EXAMPLE 14

Isomerization of Methylcyclopentane

Catalyst 1 as shaped in pellets with a diameter of 0.59 to 1.00 mm. Using this catalyst, hydroisomerization reaction of methylcyclopentane was carried out in a high pressure flow reactor with a length of 22 cm and an inner diameter of 1 cm under the following reaction conditions:

| | |
|---|---|
| Temperature | 200° C. |
| Total Pressure | 10 bar |
| H$_2$/Methylcyclopentane Molar Ratio | 5/1 mol/mol |
| Liquid Space Velocity | 1.5 ml methylcyclopentane/ml catalyst/hr |

The composition of the reactor outlet gas was analyzed by gas chromatography to obtain methycyclopentane 48 wt %, cyclohexane 24 wt % and other hydrocarbons 28 wt %.

Thus, it is apparent from this result that the catalyst of the present invention is also useful for the isomerization reaction of methylcyclopentane to cyclohexane.

EXAMPLE 15

Catalyst 35 of Example 4 was further calcined at 600° C. for 3 hours to prepare Catalyst 68, which powder was shaped in pellets with a diameter of 0.59 to 1.00 mm.

Hydroisomerization reaction of n-pentane was carried out in an analogous manner to Example 6 except using this Catalyst 68 and changing the reaction temperature to 140° C. and the H$_2$/n-pentane molar ratio to 1.5/1 mol/mol. Analysis of the reactor outlet gas was continuously carried out by gas chromatography to give compositions of; methane, ethane, propane and butane 2.5 wt %, i-pentane 72.8 wt %, n-pentane 21.2 wt % and hexane 3.4 wt % after 5 hours from the start of the reaction, and methane, ethane, propane and butane 1.0 wt %, i-pentane 72.4 wt %, n-pentane 25.4 wt % and hexane 1.1 wt % after 98 hours from the start of the reaction.

Thus, it will be apparent that the catalyst of the present invention is excellent in low temperature activity as well as durability.

What is claimed is;

1. In a method of isomerizing hydrocarbons in the presence of a catalyst, the improvement wherein the catalyst is a solid strong acid catalyst consisting essentially of a sulfate (SO$_4^{2-}$) and at least one metal selected from the group consisting of platinum, ruthenium, rhodium and palladium supported on a support consisting of at least one member selected from the group consisting of hydroxides and oxides of zirconium, wherein the sulfate is supported in a proportion of 0.1 to 7.2 parts by weight to 100 parts by weight of the support, and wherein said metal is supported in a proportion of 0.01 to 10 parts by weight to 100 parts by weight of the support, the thus supported catalyst being calcined at a temperature of 575° to 800° C.

2. In a method subjecting paraffinic hydrocarbons to skeletal isomerization on the presence of a catalyst, the improvement wherein the catalyst is a solid strong acid catalyst consisting essentially of a sulfate (SO$_4^{2-}$) and at least one metal selected from the group consisting of platinum, ruthenium, rhodium and palladium supported on a support consisting of at least one member selected from the group consisting of hydroxides and oxides of zirconium, wherein the sulfate is supported in a proportion of 0.1 to 7.2 parts by weight to 100 parts by weight of the support, and wherein said metal is supported in a proportion of 0.1 to 10 parts by weight to 100 parts by weight of the support, the thus supported catalyst being calcined at a temperature of 575° to 800° C.

* * * * *